United States Patent [19]

Becker et al.

[11] 4,331,766
[45] May 25, 1982

[54] COLLAGEN SOLUTION, PROCESS FOR ITS MANUFACTURE AND ITS USE

[75] Inventors: Udo Becker, Munich; Konrad Braun, Ebsdorfergrund; Norbert Heimburger, Marburg an der Lahn, all of Fed. Rep. of Germany

[73] Assignee: Behringwerke Aktiengesellschaft, Marburg an der Lahn, Fed. Rep. of Germany

[21] Appl. No.: 169,842

[22] Filed: Jul. 17, 1980

[30] Foreign Application Priority Data

Jul. 19, 1979 [DE] Fed. Rep. of Germany ....... 2929144

[51] Int. Cl.³ ............................................. C07G 17/00
[52] U.S. Cl. ..................... 435/273; 435/13; 435/24; 435/267
[58] Field of Search ................... 435/273, 24, 13, 265, 435/267, 268

[56] References Cited

U.S. PATENT DOCUMENTS 4,066,083 1/1978 Ries ................................ 435/273 X Primary Examiner—Robert J. Warden
Attorney, Agent, or Firm—Curtis, Morris & Safford

[57] ABSTRACT

Process for the manufacture of a collagen solution and its use for the manufacture of collagen fibrillae for adsorbing coagulation factors, as diagnostic agent, for the manufacture of a collagen sponge and for use in a cosmetic preparation.

7 Claims, No Drawings

COLLAGEN SOLUTION, PROCESS FOR ITS MANUFACTURE AND ITS USE

The present invention relates to a process for the manufacture of a collagen solution from human or animal tissue, in particular from human umbilical cords and placentae, and to its use for absorbing the coagulation factors VIII and XIII.

Processes for the manufacture of collagen are known. Moreover a very defined collagen preparation is known to be capable of binding the factor VIII antigen, while the factor VIII activity remains in the supernatant (Nyman, D., Thrombos.Research 11, (1977), 433).

Known preparations are unsuitable for the obtention of the said factors by way of a selective and quantitative absorption, for example from blood plasma. In view of the importance and the need for said coagulation factors for the treatment of disturbances in coagulation and wound healing, a collagen of the above type is of special interest, in particular for use as basic material for the manufacture of sponges.

It has now surprisingly been found that a collagen prepared under very defined conditions is capable of adsorbing the coagulation factors VIII and XIII.

The subject of the present invention therefore is a process for the manufacture of collagen, which comprises dialyzing pepin-treated collagen against a buffer solution of pH 7-8.5, preferably a phosphate-buffered isotonic salt solution of pH 7.2, containing a basic amino acid, preferably arginine, in a concentration of from 5 to 20, preferably of 10 mmols/l.

A suitable pepsin-treated collagen may be obtained in the following manner: Human or animal tissue, preferably human umbilical cords or placentae, is treated with a suitable buffer solution of pH 7-9, optionally containing neutral salts, preferably a tris-hydrochloric acid buffer of pH 7.4 containing sodium chloride and optionally a complex-forming agent, for example EDTA, citrate or phosphate, preferably EDTA and/or a proteinase inhibitor, for example a soybean trypsin or a Kunitz inhibitor, or preferably aprotinine, followed by extraction of the precipitate formed with the same buffer solution which contains no complex-forming agent and no inhibitor. The precipitate obtained upon extraction is treated with an aqueous solution of an acid of pK 3-5, preferably with a 0.5 molar acetic acid. The precipitate obtained is suspended in an aqueous solution of an acid of pK 3-5, preferably in a 0.1 molar acetic acid. The pH of the resulting suspension is brought to a value of 2, preferably with hydrochloric acid. The product is treated with pepsin, preferably for one day at 4° to 25° C., preferably at 25° C., the supernatant is separated, the residue is once more treated with pepsin, the supernatant is separated and both supernatants are combined. Next, collagen is precipitated by increasing the ionic strength by addition of a neutral salt in an amount of from 1 to 1.3 mols/l, the precipitate formed is dissolved in a buffer solution of pH 7-8.5, preferably a tris-hydrochloric acid buffer of pH 7.4 containing the neutral salt, the resulting solution is dialyzed against the same buffer and, if desired, admixed with a silicate-containing absorbent such as kaolin, or aerosil, for example Decalite speedplus (manufactured by Messrs. Degussa of Frankfurt, West Germany). Thereafter the collagen solution is separated.

When a collagen solution obtained in the above manner is heated to a temperature of at least approximately 37° C., collagen fibrillae precipitate therefrom. When heating this solution in the presence of the coagulation factors VIII and XIII, the latter factors are absorbed by the precipitating fibrillae in an active form. The temperature is chosen such that a high yield of active factors is obtained. Thus another feature of the collagen obtainable according to the process of the present invention resides in the obtention of active factors in a high yield.

The present invention is of special interest for the manufacture of concentrates of factor VIII and XIII, which are used in the therapy of certain disturbances in coagulation and wound healing. The therapy of hemophilia A with the aid of the factor VIII concentrates presently available is expensive because in the manufacture of these concentrates, for a quantity of factor VIII contained in the plasma as little as 10% is obtained. A process providing a higher yield is therefore of special interest.

The collagen preparation obtained according to the present invention can moreover be used for the manufacture of wound coverings for hemostasis, in particular in patients suffering from a pronounced tendency to hermorrhages (hemophilia), for example after tooth extractions. For this application purpose, human plasma is adsorbed on the collagen preparation, unbound plasma proportions are removed by washing and the product is lyophilized. The sponge-like collagen thus obtained contains all components which are necessary for hemostasis, for fibrin stabilization and for healing of the wound.

The collagen preparation onto which the coagulation factors are adsorbed can moreover be used as a diagnostic agent for the detection of disturbances of the platelet function. For example, when mixing blood or platelet-rich plasma of healthy persons, with a collagen preparation as obtained according to the invention, at a temperature suitable for the formation of fibrillae, the thrombocytes form clots. This reaction cannot be observed in the case of certain pathological states. Due to this spontaneous formation of fibrillae, the collagen solution is especially suitable as a diagnostic agent. However, the suspensions being used up to now cannot be standardized with a view to the size of the fibrillae.

A collagen solution or suspension of the above type is also appropriate for cosmetic purposes, especially because the collagen contained therein has a homologous structure.

TEST METHODS

Determination of the coagulation factor VIII

F VIII:C: By way of the factor VIII single phase determination using the test kit of the firm Behringwerke AG, of Marburg, West Germany, F VIII R:AG: Immunologically according to the method of Laurell, C.-B., Anal.Biochem. 10, 358 (1965), F VIII R:WF: In functional view according to the method of H.-J. Weiss et al., J.Clin.Invest. 52, 2708 (1973), using ristocetine, F XIII: By way of the factor XIII single phase determination using the rapid test of the firm Behringwerke AG, of Marburg, West Germany.

Platelet aggreation

According to Born, G. W. R., J.Physiolog. (London), 162, 67 (1962).

Immunofluorescence

According to Wick, G., Baudner, F. and Herzog, F. "Immunofluorescence", Med. Verlagsgesellschaft Marburg (1976).

Hydroxyproline determination

According to Woessner, J. F., Arch.Biochem.Biophys. 95, 440 (1961).

The present invention will be illustrated by the following examples:

EXAMPLE 1

Preparation of the collagen 10 deep-frozen umbilical cords are defrosted and cut into pieces 1 cm in length. The pieces are finely divided together with 0.5 l of extraction buffer I (0.05 m tris-HCl, pH 7.4 containing 0.5 m NaCl, 0.01 m EDTA, 250 U/l of Antagosan ®) by means of a knife homogenizer. The mixture is submitted to centrifugation and the supernatant is discarded. The remaining precipitate is stirred for 24 hours at 4° C. in 2 liters of extraction buffer I. The product is centrifuged and the supernatant is discarded. The resulting precipitate is suspended in 0.5 l of extraction buffer II which corresponds to extraction buffer I, except that is contains no Antagosan ® and after 30 minutes the resulting suspension is submitted to centrifugation, which gives a precipitate that is suspended in 0.5 l of 0.5 molar acetic acid. The resulting suspension is centrifuged after 30 minutes leaving a precipitate that is suspended in 2 liters of fresh 0.5 molar acetic acid and stirred for 24 hours at 4° C. The suspension is centrifuged and the supernatant is discarded leaving a precipitate that is suspended in 3 liters of 0.1 molar acetic acid. The resulting suspension is stirred and 1 N hydrochloric acid is added until a pH of 2 is obtained. 0.5 g of pepsin (of Messrs. Serva, 30 Anson-units per mg) is added, the product is stirred at a temperature of 25° C. for 24 hours, and subsequently centrifuged. The supernatant is retained and the residue is admixed with fresh pepsin and again decomposed as specified with a complete dissolution of the tissue of the umbilical cord taking place. Both extracts are combined and brought to a concentration of 0.9 mol/l with solid NaCl. After stirring for two hours, the product is centrifuged and the supernatant is discarded. The resulting precipitate is dissolved in 3 liters of 0.05 m tris-HCl of pH 7.4 which contains 1 mol/l of NaCl. Upon complete dissolution, the product is dialyzed for 48 hours against the same buffer in two 10 liter portions. The solution is admixed with 20 g/l of Decalite speedplus and centrifuged. The clear solution has a collagen content of 1.8 mg/ml.

1 Liter of this solution is dialyzed against two 5 liter portions of phosphate-buffered physiological saline solution of pH 7.2 (8 g/l of sodium chloride, 1.15 g/l of disodium biphosphate, 0.2 g/l of potassium dihydrogenophosphate) containing 0.01 mol/l of arginine, for 24 hours at room temperature. Subsequently a concentration of collagen of 1 mg/ml is adjusted with the dialysis buffer.

EXAMPLE 2

Five 2 ml portions of human blood plasma containing 10 volume parts of 3.8% citrate solution (as an anticoagulant) are heated to 37° C. in the water bath and increasing quantities of the collagen solution as obtained in Example 1 are added thereto, a volume equilibration being reached by adding a phosphate-buffered salt solution of pH 7.2 which contains 0.01 mol/l of arginine. The quantities of collagen added correspond to a concentration of 0, 1, 0.2, 0.5 and 1.0 mg/ml of plasma, respectively. The product is incubated for 10 minutes at 37° C. and subsequently centrifuged for 10 minutes at 1,500 g. The supernatants of the plasma and the precipitated collagen fibrillae are decanted from one another. The factor VIII activity is determined in the supernatants of the plasma. The activities of the three biological functions of the factor VIII molecule, which are the factor VIII coagulation activity (F VIII:C), the factor VIII antigen (F VIII:AG) and the v.Willebrand factor (F VIII:R:WF) are removed from the solution nearly quantitatively in the case of the maximal collagen concentration.

EXAMPLE 3

The test described in Example 2 is carried out using human blood plasma containing 4 IU of heparin/ml as an anticoagulant.

The results concerning F VIII R:AG and F VIII R:WF correspond to those obtained in Example 2. The F VIII:C cannot be determined in heparin-containing medium for methodical reasons.

EXAMPLE 4

A precipitate consisting of collagen fibrillae is prepared according to the method of Example 1 with addition of 1 mg of collagen per ml of plasma. This precipitate is washed with three 1 ml portions of physiological salt solution and subsequently suspended in a physiological salt solution in a concentration of 5 mg/ml. The comparative sample used is a suspension of collagen fibrillae of equal concentration, which has been washed in equal manner and which has been prepared by heating a corresponding volume of the collagen solution to 37° C. for 10 minutes.

Four vials each of which containing 0.1 ml of a congenital factor VIII deficiency plasma are placed in a coagulation apparatus according to Schnitger and Gross (manufactured by Messrs. H. Amelung, of 4922 Brake, West Germany) and heated to 37° C. Vial 1 contains 0.1 ml of a plasma prediluted in physiological salt solution in a ratio of 1:5 and having a normal factor VIII content. Vial 2 contains 0.1 ml of the collagen fibrillae loaded with plasma and which have been washed. Vial 3 contains 0.1 ml of the adsorbed collagen fibrillae that have not been loaded. Vial 4 contains 0.1 ml of physiological salt solution.

To each of the vials there is added 0.1 ml of a mixture of kaolin and platelet factor 3 (Pathromtin ® manufactured by Messrs. Behringwerke AG, of Marburg). The contents of the vials are mixed and subsequently incubated for 6 minutes at 37° C. Thereafter 0.1 ml of a 0.025 molar calcium chloride solution is added to each vial, whereupon the coagulation times are determined. The results are summarized in Table 1.

TABLE 1

| sample (0.1 ml) | coagulation time (sec.) |
|---|---|
| normal plasma (1:5) | 53 |
| adsorbed collagen suspension (5 mg/ml) | 66 |
| collagen suspension that has not been adsorbed (5 mg/ml) | 124 |
| buffer | 104 |

It can be seen from this table that a collagen suspension according to the invention, that has been adsorbed by normal plasma contains the biologically active coagulation factor VIII.

EXAMPLE 5

1 ml of a collagen solution is loaded with 1 ml of a citrate-containing human plasma in accordance with Example 2. The collagen fibrillae are separated by centrifugation and subsequently washed three times with a phosphate-buffered physiological saline solution. Next, the collagen fibrillae are examined for adsorbed plasma proteins with the aid of antisera of rabbits that are specific for very defined plasma proteins, by the indirect fluorescence test. Normal serum of rabbits gives a negative reaction, whereas anti-human fibrinogen, anti-human immunoglobulin and anti-human albumin give a very weak reaction. When using anti-human factor VIII serum, a very pronounced reaction can be observed.

This example demonstrates the selective and specific binding of factor VIII, which, as compared with albumin, is contained in the plasma in a concentration which is 4,400 times lower.

EXAMPLE 6

Example 6 is carried out analogously to Example 5, using, however, the plasma of a patient suffering from the v.Willebrand disease, the factor VIII concentrate of this plasma being less than 10% of the standard. The reaction of antiserum and factor VIII is very weak.

EXAMPLE 7

Human citrate plasma is adsorbed on collagen used in increasing amounts, in accordance with the procedure of Example 2. The plasma supernatants are examined for their content of factor XIII. This test is a qualitative procedure indicating the activity ranges in %, referred to normal plasma. The values obtained, as summarized in Table 2, are expressed in percentages and take into consideration the initial dilution of 1:2.

TABLE 2

| quantity of collagen (mg/ml) | factor XIII range, in % of the standard range |
|---|---|
| 0.0 | 100–150 |
| 0.1 | 75–100 |
| 0.2 | 50–75 |
| 0.5 | 25–50 |
| 1.0 | <25 |

EXAMPLE 8

1 ml of citrated platelet-rich plasma is introduced into the bulb of an aggregometer according to Born, which is equipped with a recorder (manufacturer Messrs. Braun of Melsungen, West Germany). The photometer and the recorder are adjusted to a transmission of 0%. The plasma is stirred magnetically, until the temperature has reached 37° C. 1 µl of the clear collagen solution according to Example 1, corresponding to 1 µg of collagen, is injected by a microliter syringe. An aggregation of the blood platelets can be observed within two minutes, giving great aggregates, as a consequence whereof the transmission greatly increases, this increase being traced by the recorder. This reaction is suitable for the diagnosis of coagulation disturbances.

EXAMPLE 9

The collagen solution is heated to a temperature from approximately 35° to 40° C. to make the fibrillae precipitate. The resulting gel-like product is lyophilized, yielding a stable, white collagen sponge. Factor VIII, factor XIII and/or fibrinogen may have been added to the collagen suspension before heating or may be adsorbed on the sponge from plasma, for instance.

What is claimed is:

1. A process for the preparation of a collagen solution capable of adsorbing coagulation factors VIII and XIII which comprises treating collagen-containing human or animal tissue with pepsin to form a pepsin-treated collagen and dialyzing said pepsin-treated collagen at a temperature in the range of 4° to 25° C. with a phosphate-buffered isotonic solution containing a basic amino acid at a concentration of 5 to 20 mmols/l.

2. The process of claim 1 wherein said pepsin-treated collagen is dialyzed for about 24 hours.

3. The process of claim 1 wherein said collagen-containing tissue comprises human umbilical cords or placentae.

4. The process of claim 1 wherein the basic amino acid is arginine.

5. The process of claim 1 wherein said pepsin-treated collagen is prepared by treating the collagen-containing human or animal tissue with a suitable buffer solution having a pH in the range of 7 to 9 and an aqueous solution of an acid having a pK in the range of 3 to 5 to form a suspension having a pH of about 2 and treating said suspension with pepsin at a temperature of 4° C. to 25° C. for about 24 hours to form the pepsin-treated collagen.

6. The process of claim 5 wherein said buffer solution is tris-hydrochloric acid with a pH of about 7.4 containing sodium chloride and a complex-forming agent.

7. The process of claim 5 wherein said suspension is treated with 0.5 grams of pepsin.

* * * * *